United States Patent
Roger et al.

(10) Patent No.: US 12,343,510 B1
(45) Date of Patent: *Jul. 1, 2025

(54) PREFILLED SYRINGE WITH PEGFILGRASTIM HAVING OPTIMIZED DOSE AND METHODS RELATED THERETO

(71) Applicant: FRESENIUS KABI DEUTSCHLAND GMBH, Bad Homburg (DE)

(72) Inventors: Florence Roger, Mont-sur-Rolle (CH); Fabien Vaudant, Valleiry (FR); Thierry Rimlinger, L'Isle d'Abeau (FR); Christian Ebert, Frankfurt (DE); Rodrigue Chatton, Echichens (CH); Alexander Degen, Bad Homburg (DE); Kevin Reitz, Florstadt (DE); Torsten Brandenburger, Reichelsheim (DE)

(73) Assignee: FRESENIUS KABI DEUTSCHLAND GMBH, Bad Homburg (DE)

( * ) Notice: Subject to any disclaimer, the term of this patent is extended or adjusted under 35 U.S.C. 154(b) by 60 days.

This patent is subject to a terminal disclaimer.

(21) Appl. No.: 18/107,386

(22) Filed: Feb. 8, 2023

Related U.S. Application Data (63) Continuation of application No. 17/198,404, filed on Mar. 11, 2021, now Pat. No. 11,602,598.

(60) Provisional application No. 63/071,228, filed on Aug. 27, 2020.

(51) Int. Cl.
| | |
|---|---|
| *C07K 14/535* | (2006.01) |
| *A61K 38/19* | (2006.01) |
| *A61K 47/10* | (2017.01) |
| *A61M 5/178* | (2006.01) |
| *A61M 5/31* | (2006.01) |
| *A61M 5/315* | (2006.01) |
| *A61K 38/18* | (2006.01) |

(52) U.S. Cl.
CPC ....... *A61M 5/31525* (2013.01); *A61K 38/193* (2013.01); *A61K 47/10* (2013.01); *A61M 5/178* (2013.01); *A61M 5/3129* (2013.01); *C07K 14/535* (2013.01); *A61K 38/18* (2013.01); *A61M 2005/3114* (2013.01); *A61M 2005/31516* (2013.01); *A61M 2202/0007* (2013.01); *A61M 2207/10* (2013.01)

(58) Field of Classification Search
CPC ...... A61K 38/19; A61K 38/18; A61K 38/193; C07K 14/52; C07K 14/535; C07K 14/53; A61M 5/3129; A61M 5/178; A61M 2005/31516; A61M 2207/10; A61M 5/31525; A61M 2005/3114

See application file for complete search history.

(56) References Cited

U.S. PATENT DOCUMENTS

| | | | |
|---|---|---|---|
| 5,824,784 | A | 10/1998 | Kinstler et al. |
| 7,632,247 | B2 | 12/2009 | Adams |
| 7,678,079 | B2 | 3/2010 | Shermer et al. |
| 7,771,412 | B2 | 8/2010 | Anderson et al. |
| 9,061,097 | B2 | 6/2015 | Holt et al. |
| 9,402,950 | B2 | 8/2016 | Dilanni et al. |
| 2015/0258284 | A1 | 9/2015 | Fenster et al. |
| 2016/0038689 | A1 | 2/2016 | Lee et al. |
| 2016/0121043 | A1 | 5/2016 | Weibel et al. |
| 2017/0184091 | A1 | 6/2017 | Focht et al. |
| 2018/0099087 | A1 | 4/2018 | Cole et al. |
| 2018/0105294 | A1* | 4/2018 | Abboud .................. B65B 3/003 |
| 2018/0272058 | A1 | 9/2018 | Pizzochero et al. |
| 2019/0022317 | A1 | 1/2019 | Uddin et al. |
| 2020/0001006 | A1 | 1/2020 | Pizzochero et al. |
| 2020/0069873 | A1 | 3/2020 | Pizzochero et al. |

FOREIGN PATENT DOCUMENTS

| | | |
|---|---|---|
| WO | 2016209554 A1 | 12/2016 |
| WO | 2019005072 A1 | 1/2019 |

OTHER PUBLICATIONS

Gangane et al. Delivering Biologics in Prefilled Syringes: An innovation in parenteral packaging. J Pharmacy Res Technol 10(1): 58-66, Jan.-Jun. 2020.*

Neulasta Onpro Kit Healthcare Provider Instructions for Use, http://web.archive.org/web/20171025234748/http://pi.amgen.com/~/media/amgen/repositorysites/pi-amgen-com/neulasta/neulasta_ifu_hcp_pt_old_english.pdf; pdf dated Apr. 2016; Wayback machine capture Oct. 25, 2017.*

Neulasta Onpro Kit Website, http://web.archive.org/web/20180713022131/https://www.neulastahcp.com/, 2018.*

BD Hypak SCF(TM) PRTC Glass Pre-Fillable Syringe-BD, printed from https://drugdeliverysystems.bd.com/products-and-services/products/prefillable-syringe-systems/acute-care-and-specialty-syringes/hypak-scf-prtc-glass%E2%80%A6 on Jan. 29, 2021, 4 pages.

BD Neopak Information Guide; https://drugdeliverysystems.bd.com/a/86758; May 14, 2020; 34 total pages.

Declaration Under 37 C.F.R. 1.132 by Dr. Alexander Degen dated Nov. 3, 2022 and Attached Report, 7 pages.

Defy Medical Low Dead Space Syringe article; https://www.defymedical.com/blog/new-low-dead-space-syringes-available-at-defy-medical; Feb. 19, 2012; two total pages.

(Continued)

*Primary Examiner* — Bridget E Bunner
(74) *Attorney, Agent, or Firm* — Becker Patent Law, LLC (57) ABSTRACT

A prefilled syringe and a method of filling a syringe with a pegfilgrastim solution to provide a target extracted volume of pegfilgrastim solution from the syringe are described. A method includes selecting the target extracted volume of pegfilgrastim solution, determining an estimated drug transfer loss, determining an estimated syringe dead volume, filling the syringe with a volume of pegfilgrastim solution comprising at least the target extracted volume plus the estimated drug transfer loss plus the estimated syringe dead volume.

5 Claims, 11 Drawing Sheets

(56) References Cited

OTHER PUBLICATIONS

Harrison et al. Big Shot: Developments in prefilled syringes. Pharmaceut Technol 31(3): pp. 50, 52, 54, 56, 58, 60; Mar. 2007.

Highlights of Prescribing Information, Full Prescribing Information, Neulasta (R) (pegfilgrastim), (c)2002-2019 Amgen Inc., 15 pages, Apr. 2019.

Jordan, M. Dosing errors related to improper use of syringes: Dead space and technique. J Nursing Care 2: 3, p. 27, 2013.

Neulasta (R) (pegfilgrastim) Onpro (R) kit Healthcare Provider Instructions for Use, 12 pages. Metadata: Created Apr. 22, 2020.

Neulasta Product Monograph; https://pdf.hres.ca/dpd_pm/00039226.PDF; Jan. 13, 2017; 27 total pages.

No Author Provided. Manufacturing Chemist. "Pre-filled syringes: trends and tips from the experts". May 5, 2015, www.manufacturingchemist.com/news/article_page/Pre-filled_syringes_trends_and_tips_from_the_experts/108087.

Pharmaceutical Technology Editors, Equipment and Processing Report, "Stoppering Techniques for Prefilled Syringes", https://www.pharmtech.com/view/stoppering-techniques-prefilled-syringes; Dec. 17, 2008.

Piedmonte et al. Formulation of Neulasta (pegfilgrastim). Advanced Drug Delivery Rev 60: 50-58, 2008.

Sacha et al. Pre-filled syringes: a review of the history, manufacturing and challenges. Pharm Dev Technol 20(1): 1-11, 2015.

Siew, A. Drug-delivery systems for biopharmaceuticals. BioPharm Int pp. 14-19, Aug. 2015.

SyriQ BioPure (R) Schott AG, printed from https://www.schott.com/pharmaceutical_packaging/english/products/syringes/glass_syringes/syriq-biopure.html on Jan. 29, 2021, 3 pages.

Treating Febrile Neutropenia Neulasta (R) (pegfilgrastim Onpro (R), printed from https://www.neulasta.com on Jan. 29, 2021, 6 pages.

Wright et al. Prefillable Syringe Technology—BD Neopak—delivering the next generation in glass prefillable syringes. Drug Develop Delivery Jan./Feb. 2014 (https://drug-dev.com/prefillable-syringe-technology-bd-neopak-delivering-the-next-generation-in-glass-prefillable-syringes/).

Yang et al. Comparison of pharmacokinetics and safety of pegfilgrastim administered by two delivery methods: on-body injector and manual injection with a prefilled syringe. Cancer Chemother Pharmacol 75: 1199-1206, 2015.

\* cited by examiner

FIG. 1

| NO. | TEST | METHOD/STANDARD | DESCRIPTION/CONDITION | SOLUTION | AMOUNT |
|---|---|---|---|---|---|
| 1 | DA-CLIMATIC | 11608-1 | 10 X 5°C; 10 X 23°C; 10 X 40°C EXTENDED DA TEST PROCEDURE | DP | 30 |
| 2 | DA-DROP TEST | 11608-1 | DROP TEST; 6 ORIENTATIONS X 5 | DP | 30 |
| 3 | DA-CLIMATIC | CHALLENGING TEST 1 | 23°C, TRY TO MANIPULATE THE DEVICE | DP | 5 |
| 4 | DA-ORIENTATION | CHALLENGING TEST 2 | IMPACT OF DIFFERENT INJECTOR ORIENTATIONS/ANGLES ON DA (5X5) | DP | 25 |
| 5 | DA-FILLING SPEED | CHALLENGING TEST 3 | IMPACT OF DIFFERENT FILLING SPEEDS ON FUNCTION | DP | 10 |

FIG. 2

| DRUG TRANSFER LOSS (ml) | REMARK |
|---|---|
| 0.0007 | NO DROP |
| 0.0049 | DROPS |
| 0.0003 | NO DROP |
| 0.0060 | DROPS |
| 0.0007 | NO DROP |
| 0.0015 | DROPS |
| 0.0053 | DROPS |
| 0.0056 | DROPS |
| 0.0061 | DROPS |
| 0.0061 | DROPS |
| 0.0027 | DROPS |
| 0.0002 | NO DROP |

FIG. 3

| | PFS FILLING VOLUME (ml) | PFS EXTRACTED VOLUME (ml) | PFS DEAD VOLUME (ml) |
|---|---|---|---|
| # | 77 | 77 | 77 |
| $\bar{x}$ | 0,6469 | 0,6422 | 0,0020 |
| $\sigma$ | 0,0021 | 0,0047 | 0,0013 |
| MIN | 0,6434 | 0,6244 | 0,0006 |
| MAX | 0,6590 | 0,6564 | 0,0085 |

PFS FILL VOLUME MEETS TARGET FILL VOLUME 0,645 mL

PFS EXTRACTED VOLUME CAN BE IMPACTED DUE TO TRANSFER DRUG LOSS

FIG. 4

| | n | INJECTOR DELIVERY (ml) | INJECTOR DEAD VOLUME (ml) | INJECTOR FILLING VOLUME (ml) | INJECTOR DELIVERY EFFICIENCY (%) | PFS EXTRACTED VOLUME (ml) | DRUG TRANSFER LOSS (ml) |
|---|---|---|---|---|---|---|---|
| #1 CLIMATIC, 23°C | 9 | 0,6131 | 0,0227 | 0,6360 | 96,40% | 0,6427 | 0,0067 |
| #1 CLIMATIC, 5°C | 8 | 0,6213 | 0,0157 | 0,6370 | 97,53% | 0,6419 | 0,0049 |
| #1 CLIMATIC, 40°C | 11 | 0,6199 | 0,0223 | 0,6407 | 96,76% | 0,6443 | 0,0036 |
| #2 DROP TEST | 30 | 0,6165 | 0,0194 | 0,6364 | 96,87% | 0,6404 | 0,0040 |
| #4 ORIENTATION | 14 | 0,6190 | 0,0232 | 0,6433 | 96,22% | 0,6439 | 0,0006 |
| #5 FILLING SPEED | 5 | 0,6270 | 0,0144 | 0,6423 | 97,62% | 0,6432 | 0,0009 |

FIG. 5

| | n | INJECTOR DELIVERY (ml) | INJECTOR DEAD VOLUME (ml) | INJECTOR FILLING VOLUME (ml) | INJECTOR DELIVERY EFFICIENCY (%) | PFS EXTRACTED VOLUME (ml) | DRUG TRANSFER LOSS (ml) |
|---|---|---|---|---|---|---|---|
| CLIMATIC, 23°C  x̄ | 9 | 0,6131 | 0,0227 | 0,6360 | 96,40% | 0,6427 | 0,0067 |
| σ | 9 | 0,0054 | 0,0041 | 0,0055 | 0,66% | 0,0024 | 0,0043 |
| MIN | 9 | 0,6017 | 0,0173 | 0,6307 | 95,07% | 0,6385 | 0,0007 |
| MAX | 9 | 0,6194 | 0,0288 | 0,6465 | 97,09% | 0,6472 | 0,0131 |
| CLIMATIC, 5°C  x̄ | 8 | 0,6213 | 0,0157 | 0,6370 | 97,53% | 0,6419 | 0,0049 |
| σ | 8 | 0,0104 | 0,0049 | 0,0104 | 0,76% | 0,0045 | 0,0063 |
| MIN | 8 | 0,6057 | 0,0081 | 0,6204 | 96,63% | 0,6324 | -0,0013 |
| MAX | 8 | 0,6353 | 0,0211 | 0,6475 | 98,70% | 0,6464 | 0,0128 |
| CLIMATIC, 40°C  x̄ | 11 | 0,6199 | 0,0223 | 0,6407 | 96,76% | 0,6443 | 0,0036 |
| σ | 11 | 0,0086 | 0,0042 | 0,0059 | 0,69% | 0,0048 | 0,0073 |
| MIN | 11 | 0,6025 | 0,0170 | 0,6269 | 95,54% | 0,6362 | -0,0007 |
| MAX | 11 | 0,6337 | 0,0319 | 0,6466 | 98,01% | 0,6564 | 0,0240 |

FIG. 6

| DROP ORIENTATION | | n | INJECTOR DELIVERY (ml) | INJECTOR DEAD VOLUME (ml) | INJECTOR FILLING VOLUME (ml) | INJECTOR DELIVERY EFFICIENCY (%) | PFS EXTRACTED VOLUME (ml) | DRUG TRANSFER LOSS (ml) |
|---|---|---|---|---|---|---|---|---|
| HORIZONTAL 1 | $\bar{x}$ | 5 | 0,6145 | 0,0212 | 0,6364 | 96,54% | 0,6393 | 0,0029 |
| | σ | 5 | 0,0109 | 0,0035 | 0,0083 | 0,61% | 0,0063 | 0,0031 |
| | MIN | 5 | 0,6006 | 0,0169 | 0,6268 | 95,64% | 0,6300 | 0,0002 |
| | MAX | 5 | 0,6246 | 0,0263 | 0,6429 | 97,29% | 0,6448 | 0,0078 |
| HORIZONTAL 2 | $\bar{x}$ | 5 | 0,6155 | 0,0181 | 0,6341 | 97,06% | 0,6390 | 0,0048 |
| | σ | 5 | 0,0066 | 0,0016 | 0,0077 | 0,24% | 0,0062 | 0,0034 |
| | MIN | 5 | 0,6056 | 0,0170 | 0,6233 | 96,64% | 0,6320 | 0,0009 |
| | MAX | 5 | 0,6221 | 0,0210 | 0,6437 | 97,26% | 0,6446 | 0,0092 |
| VERTICAL 1 | $\bar{x}$ | 5 | 0,6163 | 0,0180 | 0,6345 | 97,12% | 0,6367 | 0,0021 |
| | σ | 5 | 0,0126 | 0,0055 | 0,0106 | 0,88% | 0,0094 | 0,0014 |
| | MIN | 5 | 0,5980 | 0,0112 | 0,6215 | 96,22% | 0,6244 | 0,0008 |
| | MAX | 5 | 0,6317 | 0,0235 | 0,6434 | 98,19% | 0,6450 | 0,0042 |
| VERTICAL 2 | $\bar{x}$ | 5 | 0,6135 | 0,0208 | 0,6349 | 96,62% | 0,6417 | 0,0067 |
| | σ | 5 | 0,0090 | 0,0032 | 0,0082 | 0,52% | 0,0051 | 0,0044 |
| | MIN | 5 | 0,6023 | 0,0155 | 0,6245 | 96,21% | 0,6336 | 0,0010 |
| | MAX | 5 | 0,6205 | 0,0237 | 0,6437 | 97,49% | 0,6472 | 0,0126 |
| VERTICAL 3 | $\bar{x}$ | 5 | 0,6181 | 0,0185 | 0,6373 | 97,00% | 0,6416 | 0,0043 |
| | σ | 5 | 0,0066 | 0,0039 | 0,0072 | 0,58% | 0,0048 | 0,0048 |
| | MIN | 5 | 0,6072 | 0,0120 | 0,6285 | 96,55% | 0,6337 | 0,0003 |
| | MAX | 5 | 0,6235 | 0,0219 | 0,6454 | 97,98% | 0,6458 | 0,0119 |
| VERTICAL 4 | $\bar{x}$ | 5 | 0,6212 | 0,0197 | 0,6411 | 96,90% | 0,6443 | 0,0032 |
| | σ | 5 | 0,0059 | 0,0053 | 0,0037 | 0,86% | 0,0024 | 0,0034 |
| | MIN | 5 | 0,6167 | 0,0123 | 0,6374 | 95,94% | 0,6407 | 0,0003 |
| | MAX | 5 | 0,6295 | 0,0256 | 0,6464 | 98,13% | 0,6471 | 0,0084 |

FIG. 7

| ORIENTATION | | n | INJECTOR DELIVERY (ml) | INJECTOR DEAD VOLUME (ml) | INJECTOR FILLING VOLUME (ml) | INJECTOR DELIVERY EFFICIENCY (%) | PFS EXTRACTED VOLUME (ml) | DRUG TRANSFER LOSS (ml) |
|---|---|---|---|---|---|---|---|---|
| VERTICAL 1 | x̄ | 3 | 0,6158 | 0,0267 | 0,6431 | 95,76% | 0,6441 | 0,0010 |
| | σ | 3 | 0,0086 | 0,0077 | 0,0008 | 1,22% | 0,0012 | 0,0004 |
| | MIN | 3 | 0,6096 | 0,0179 | 0,6423 | 94,90% | 0,6431 | 0,0007 |
| | MAX | 3 | 0,6256 | 0,0322 | 0,6439 | 97,15% | 0,6454 | 0,0014 |
| VERTICAL 2 | x̄ | 3 | 0,6203 | 0,0233 | 0,6440 | 96,31% | 0,6447 | 0,0007 |
| | σ | 3 | 0,0061 | 0,0046 | 0,0017 | 0,70% | 0,0017 | 0,0002 |
| | MIN | 3 | 0,6159 | 0,0180 | 0,6425 | 95,87% | 0,6433 | 0,0004 |
| | MAX | 3 | 0,6272 | 0,0262 | 0,6458 | 97,12% | 0,6466 | 0,008 |
| VERTICAL 3 | x̄ | 3 | 0,6207 | 0,0226 | 0,6437 | 96,42% | 0,6442 | 0,0004 |
| | σ | 3 | 0,0036 | 0,0032 | 0,0030 | 0,50% | 0,0031 | 0,0033 |
| | MIN | 3 | 0,6177 | 0,0203 | 0,6404 | 95,86% | 0,6413 | -0,0031 |
| | MAX | 3 | 0,6247 | 0,0263 | 0,6464 | 96,77% | 0,6475 | 0,0033 |
| VERTICAL 4 | x̄ | 3 | 0,6217 | 0,0201 | 0,6426 | 96,75% | 0,6428 | 0,0003 |
| | σ | 3 | 0,0016 | 0,0009 | 0,0012 | 0,16% | 0,0014 | 0,0008 |
| | MIN | 3 | 0,6203 | 0,0193 | 0,6414 | 96,56% | 0,6417 | -0,0007 |
| | MAX | 3 | 0,6233 | 0,0211 | 0,6439 | 96,87% | 0,6444 | 0,0009 |

FIG. 8

| | n | INJECTOR DELIVERY (ml) | INJECTOR DEAD VOLUME (ml) | INJECTOR FILLING VOLUME (ml) | INJECTOR DELIVERY EFFICIENCY (%) | PFS EXTRACTED VOLUME (ml) | DRUG TRANSFER LOSS (ml) |
|---|---|---|---|---|---|---|---|
| x̄ | 5 | 0,6270 | 0,0144 | 0,6423 | 97,62% | 0,6432 | 0,0009 |
| σ | 5 | 0,0029 | 0,0026 | 0,0007 | 0,49% | 0,0010 | 0,0008 |
| MIN | 5 | 0,6221 | 0,0119 | 0,6416 | 96,80% | 0,6419 | 0,0003 |
| MAX | 5 | 0,6291 | 0,0186 | 0,6432 | 98,02% | 0,6444 | 0,0022 |

FIG. 9

| | INJECTOR PFS (ml) | STANDALONE PFS (ml) |
|---|---|---|
| x̄ | 0.6182 | 0.6183 |
| σ | 0.0082 | 0.0038 |
| MIN | 0.5980 | 0.6106 |
| MAX | 0.6353 | 0.6232 |

FIG. 10

| TECHNOLOGY | | $PFS_i$ (g) W/O CAP | $PFS_e$ (g) | PFS EXTRACTED DRUG WEIGHT (g) | $PFS_{d24}$ (g) | PFS EXTRACTED VOLUME (ml) | PFS DEAD VOLUME (ml) | PFS FILLING VOLUME (ml) | DRUG TRANSFER LOSS (ml) |
|---|---|---|---|---|---|---|---|---|---|
| | # | 18 | 18 | 18 | 18 | 18 | 18 | 18 | 18 |
| | x̄ | 12.6760 | 12.0456 | 0.6295 | 12.0419 | 0.6183 | 0.0036 | 0.6229 | 0.0045 |
| | σ | 0.0306 | 0.0312 | 0.0039 | 0.0306 | 0.0038 | 0.0015 | 0.0033 | 0.0017 |
| | MIN | 12.6162 | 11.9831 | 0.6216 | 11.9792 | 0.6106 | 0.0004 | 0.6146 | 0.0022 |
| | MAX | 12.7236 | 12.0927 | 0.6344 | 12.0886 | 0.6232 | 0.0068 | 0.6278 | 0.0085 |

PREFILLED SYRINGE WITH PEGFILGRASTIM HAVING OPTIMIZED DOSE AND METHODS RELATED THERETO

CROSS-REFERENCE TO RELATED APPLICATIONS

This application is a continuation of prior application Ser. No. 17/198,404, filed Mar. 11, 2021, which claims the benefit of U.S. Provisional Application No. 63/071,228, filed Aug. 27, 2020. U.S. application Ser. No. 17/198,404, filed Mar. 11, 2021 is incorporated by reference herein in its entirety.

BACKGROUND

1. Technical Field

This document relates to a prefilled syringe having an optimized dose of a medicament and various methods relating thereto For example, this document relates to pre-filled syringes containing a proper volume of a pegfilgrastim solution for administering a dose through use of injection devices such as autoinjectors, infusion pumps, other injectors, etc.

2. Background Information

Injection devices come in a variety of forms. An autoinjector can receive a prefilled syringe and be used by a clinician or patient to trigger a drive to inject a medicament from the prefilled syringe under bias of a spring or motor. Infusion pumps can receive a prefilled syringe or be filled by a syringe and dispense medicament to a patient under control of a control circuit. On-body injection devices, worn on a skin surface of a patient, can provide patients with a convenient means for receiving liquid pharmaceutical agents at the proper dosage and the proper timing.

SUMMARY

In one embodiment, a method of filling a syringe with a pegfilgrastim solution to provide a target extracted volume of pegfilgrastim solution from the syringe includes selecting the target extracted volume of pegfilgrastim solution, determining an estimated drug transfer loss, determining an estimated syringe dead volume, filling the syringe with a volume of pegfilgrastim solution comprising at least the target extracted volume plus the estimated drug transfer loss plus the estimated syringe dead volume.

In some embodiments, the method may comprise determining an estimated syringe gas volume and subtracting the estimated syringe gas volume from the volume of pegfilgrastim solution that is filled into the syringe.

In some embodiments, the volume of pegfilgrastim solution filled into the syringe is 645 to 650 microliters.

In some embodiments, the target extracted volume of pegfilgrastim solution is 640 microliters to 644 microliters.

In some embodiments, the pegfilgrastim solution is an aqueous solution comprising about 10 mg/ml pegfilgrastim, 10 mM acetate, 5 wt. % sorbitol, and 0.0004 wt. % polysorbate 20.

In another embodiment, a method of making a prefilled syringe comprising providing a syringe having a barrel and filling the barrel with a pegfilgrastim solution to a volume of 645 microliters to 650 microliters.

In some embodiments, the syringe has a dead volume of between 0.6 and 8.5 microliters.

In some embodiments, the syringe has a dead volume of about 2 microliters.

In another embodiment, a method of filling a device from a prefilled syringe comprises providing a prefilled syringe having a barrel, stopper and plunger, the barrel containing 645 to 650 microliters of pegfilgrastim solution and moving the plunger and stopper to expel the pegfilgrastim solution into the device.

In some embodiments, at least 624 microliters are expelled into the device.

In some embodiments, at least 642 microliters are expelled into the device.

This document describes devices and methods for dose optimization of injector systems that deliver liquid pharmaceutical agents. For example, this document describes pre-filled syringes containing a proper volume of a pegfilgrastim solution for filling an injector so that the injector delivers an accurate bolus dosage of the pegfilgrastim to treat a patient. An accurate bolus dosage of pegfilgrastim may provide equivalent pharmacokinetic and pharmacodynamic properties for this mode of administration compared to a direct administration via a pre-filled syringe.

Particular embodiments of the subject matter described in this document can be implemented to realize one or more of the following advantages. In some embodiments, the devices and methods described herein can be used to help ensure that an injection device is filled with a target volume of a pegfilgrastim solution so that a patient using the injection device is injected with an accurate bolus dosage of the pegfilgrastim. For example, a pre-filled syringe containing an initial volume of pegfilgrastim can be used to fill the injection device with the target volume of pegfilgrastim. As described further herein, the initial volume of pegfilgrastim that is pre-loaded in the pre-filled syringe can be precisely determined to account for losses and inefficiencies associated with the overall injection system and filling process.

As used herein, the term "pegfilgrastim" refers to pegfilgrastim and biosimilars thereof.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DETAILED DESCRIPTION OF ILLUSTRATIVE EMBODIMENTS

This document describes devices and methods for dose optimization of injector systems that deliver liquid pharmaceutical agents. For example, this document describes pre-filled syringes containing an initial volume of a pegfilgrastim solution for filling a bolus-delivering injector so that the injector delivers an accurate bolus dosage of the pegfilgrastim to treat a patient. An accurate bolus dosage may provide equivalent or similar pharmacokinetic and pharmacodynamic properties for this mode of administration compared to a direct administration via a pre-filled syringe.

Figure 1:
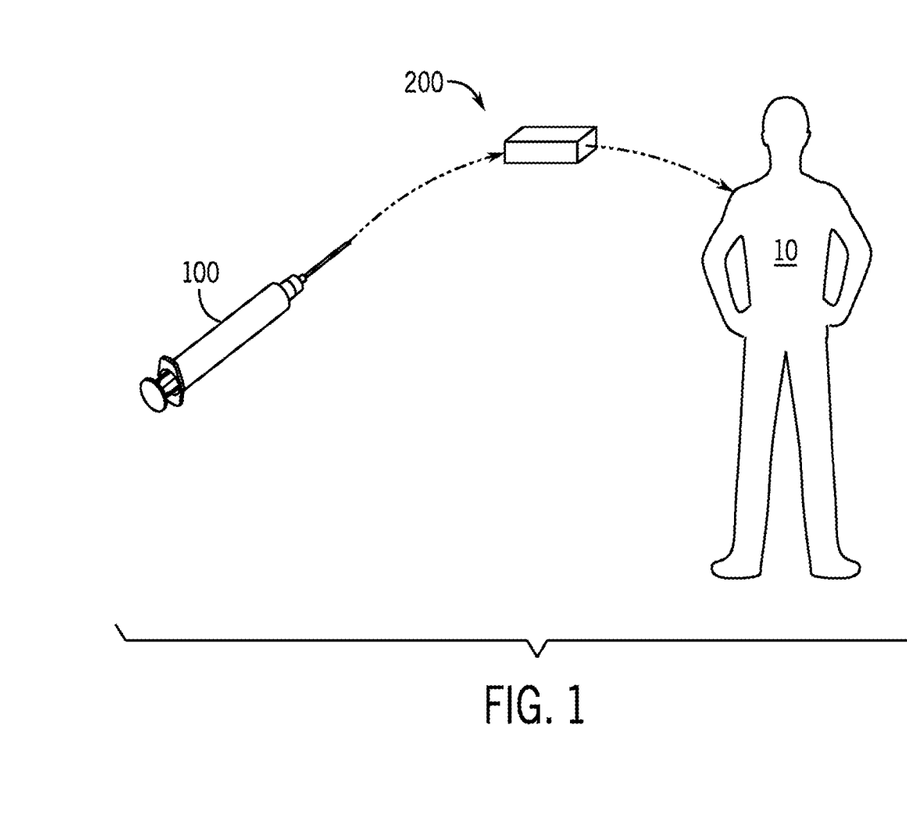
FIG. 1 is a schematic diagram of a patient and an injection system in accordance with some embodiments provided herein.

As illustrated in FIG. 1, a patient 10 can be treated using an injection system that includes a pre-filled syringe ("PFS") 100 and an injection device 200. In general, the PFS 100 is used to fill the injector device 200 with a volume of pegfilgrastim, and then the injector device 200 is used to administer the pegfilgrastim to patient 10. The pegfilgrastim may be formulated as an aqueous solution containing 10 mg/ml pegfilgrastim, 10 mM acetate, 5 wt. % sorbitol, and 0.0004 wt. % polysorbate 20.

Any of a variety of syringes may be used. Syringes may be prefilled, such as during manufacturing, or not prefilled and filled by a clinician from a vial prior to use. In one embodiment, the syringe may be a Hypak SCF PRTC 27GA1/2 IN-SBEV RNS7974 LW, glass pre-fillable syringe manufactured by Becton-Dickinson of Vernon Hills, Illinois. In another embodiment, the syringe may be a Schott syriQ BioPure Syringe Model 1752784, 1 ml long/Staked Needle 29½" with RNS Stelmi 4800GS, Cut Flange, manufactured by Schott AG, Mainz, Germany. The syringe may comprise a coated plunger stopper having a plurality of ribs for sealing engagement with an interior of a syringe body. The syringe may comprise a removable rigid needle shield. The syringe may comprise a tip cap design having a twist-off mechanism.

In some embodiments, the dose delivered to the patient 10 is substantially dependent on the volume of the pegfilgrastim filled into the injector device 200 from the PFS 100, as well as the concentration of pegfilgrastim. For example, in some embodiments the injector device 200 is configured to deliver as much of the pegfilgrastim as it possibly can (save for some dead volume or dead space within the injector device 200, as described further below). Accordingly, since the PFS 100 is used to fill the pegfilgrastim into the injector device 200, the volume of the pegfilgrastim transferred from the PFS 100 to the injector device 200 is a primary controller of the actual dosage delivered to the patient 10 by the injector device 200.

In the depicted configuration, the injector device 200 is currently empty. That is, the injector device 200 does not yet contain any volume of pegfilgrastim. In contrast, the PFS 100 contains a particular volume of pegfilgrastim. The pegfilgrastim contained in the PFS 100 is intended for transfer into the injector device 200.

In some cases, the contents of the PFS 100 will be substantially emptied into the injector device 200. That is, with the PFS 100 fluidly coupled to the injector device 200, a user (e.g., a nurse or other type of clinician) will push the plunger of the PFS 100 as far as it can travel to inject as much of the pegfilgrastim into the injector device 200 as possible. However, even when the plunger of the PFS 100 is moved to its fullest extent, a small residual volume of the pegfilgrastim can remain in the PFS 100 (e.g., remaining in the needle of the PFS 100 or the Luer cone in the case of a syringe having a Luer connection, etc.). The space(s) containing such residual volumes of pegfilgrastim remaining in the PFS 100 is hereafter referred to as the "PFS dead volume." Accordingly, in order to fill the injector device 200 to a desired volume (to ensure the proper dosage is delivered to the patient 10 by the injector device 200), the PFS dead volume should be taken into consideration when determining an initial volume for filling the PFS 100.

A PFS is generally filled with liquid and some small amount of gas. This causes some variability in the volume of drug remaining in a container when emptied, since some of the dead volume may be occupied by gas, not the pegfilgrastim solution. Dead volume can refer to the maximum volume of liquid that can remain in the container after it has been emptied. Residual volume of liquid can refer to the volume of liquid that actually remains in the container.

Even prior to the transfer of the pegfilgrastim from the PFS 100 to the injector device 200, some volume of the pegfilgrastim in the PFS 100 may be expended or lost. For example, the user of the PFS 100 may take actions such as priming the PFS 100 or eliminating air bubbles from within the PFS 100. Such actions may cause pegfilgrastim losses referred to hereafter as "drug transfer loss." Drug transfer loss can occur on PFS cap removal and/or when turning the PFS upside down to fill an injector. Accordingly, in order to fill the injector device 200 to a target volume (to ensure the proper dosage is delivered to the patient 10 by the injector device 200), the drug transfer losses should be taken into consideration when determining a target volume for filling the PFS 100.

Like the PFS, the injector device may have an injector dead volume. The injector dead volume may comprise a residual volume of pegfilgrastim after complete injection and a small amount of gas, or no gas in which case the actual residual volume of pegfilgrastim is equal to the portion of the injector dead volume. Injector dead volume can occur at various locations on the injector.

Such locations at which residual amounts of the pegfilgrastim may remain in the injector device 200 (after a fully completed activation of the injector device 200) make up additional portions of the injector dead volume. Accordingly, in order to fill the injector device 200 to a desired volume (to ensure the proper dosage is delivered to the patient 10 by the injector device 200), the injector dead volume and/or injector residual volume should be taken into consideration when determining a target volume for filling the PFS 100.

In view of the foregoing descriptions, it can be understood that Equation 1 below applies when filling the PFS 100 with pegfilgrastim to ensure the proper dosage of pegfilgrastim is delivered to the patient 10 by the injector device 200.

$$\text{PFS FV} = \text{Volume\_to\_be\_injected} + \text{DTL} + \text{PFS}_{RV} + \text{INJECTOR}_{RV} \quad \text{Equation 1}$$

Where:
a) "PFS FV" is the target volume of pegfilgrastim to be filled into the PFS;
b) "Volume_to_be_injected" is the prescribed or proper dosage of pegfilgrastim to be injected into the patient;
c) "DTL" is the drug transfer loss;
d) "$\text{PFS}_{RV}$" is the residual volume of pegfilgrastim solution in the PFS; and
e) "$\text{INJECTOR}_{RV}$" is the residual volume of pegfilgrastim solution in the injector.

The ratios of $PFS_{RV}/PFS_{DV}$ ($PFS_{DV}$=prefilled syringe dead volume) and $INJECTOR_{RV}/INJECTOR_{DV}$ (on-body injector dead volume) are variable and may depend on the surface tension of the pegfilgrastim solution, the surface tensions of the materials enclosing the dead volumes, the volume of gas in the dead volumes and the speed of injection/flushing of liquid through the dead volumes.

The values of DTL, $PFS_{RV}$, $PFS_{DV}$, $INJECTOR_{RV}$, and $INJECTOR_{DV}$ can be measured, estimated, or calculated using a number of different techniques. In one example, the volumes of one or more components of the fluid path of the injector can be determined from part specifications and/or measurements. In another example, empirical testing can be done on a plurality of samples of PFSs and injectors to determine the quantities of pegfilgrastim remaining after the various manipulations or operations, such as filling the PFS, expelling from the PFS, filling the injector, expelling from the injector, etc. The volumes can be determined by weighing the PFS and injector samples before and after the manipulations to determine the weight difference and converting the weight difference into a volume.

In one embodiment, the proper dosage to be delivered may be about 600 microliters (uL). In another embodiment, the proper dosage to be delivered may be between about 595 uL and 605 uL.

In some embodiments, PFS FV may further comprise an overfill amount (OVF). The OVF amount may be an amount of a pharmaceutical drug to provide greater assurance that the labeled dose is being delivered, and not less, as may be required by local pharmaceutical regulations. For example, an overfill amount of 20 uL may be added to the PFS FV calculated in Equation 1 above to achieve a nominal dose of at least 600 uL (6 mg of a 10 mg/ml pegfilgrastim solution). In other embodiments, other overfill amounts may be added to the PFS FV calculation of Equation 1, such as at least or about 5 uL, at least or about 10 uL, at least or about 15 uL, at least or about 20 uL, etc. In some embodiments, the overfill amount may be less than or about 20 uL, less than or about 15 uL, less than or about 10 uL, or less than or about 5 uL.

EXAMPLE

Full dose accuracy testing was conducted to determine whether a PFS FV of 645 microliters (uL) would deliver an accurate bolus dose (volume to be injected) of 620 uL to a patient via an injector. 620 uL may be a bolus dose for achieving a desired pharmacokinetic/pharmacodynamic result in a patient, according to one embodiment.

Figure 2:
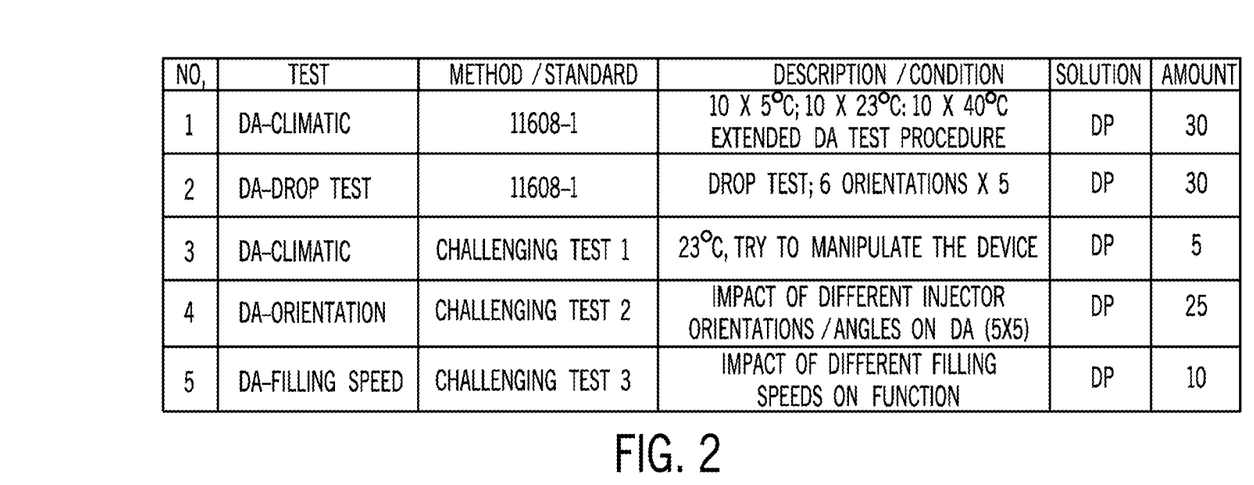
FIGS. 2-11 are tables showing results of testing conducted to determine, among other things, an initial fill volume of a PFS for use with an injector to achieve an accurate bolus dosage to the patient, according to illustrative embodiments.

FIG. 2 is a table showing five tests which were conducted. In total, 100 samples were tested under select conditions and the impact on the bolus dose delivered was determined. A first test was conducted using the ISO 11608-1 test standard. Injectors were filled, each from an associated PFS. 10 injectors were filled at each of 5 degrees C., 23 degrees C. and 50 degrees C. The second test was conducted using the ISO 11608-1 drop test in which filled injectors were dropped from six different orientations prior to filling from the PFS. The third test was conducted on five injectors, a climatic test at 23 degrees C. while trying to manipulate the device. The fourth test was an orientation test to test the impact of different injector orientations/angles in which the injector was disposed on the target patient during injection. Five syringes were tested at each of five orientations. A fifth test looked at the filling speed of the injector from the PFS to determine the impact of filling speed on the delivery dose.

Figure 3:
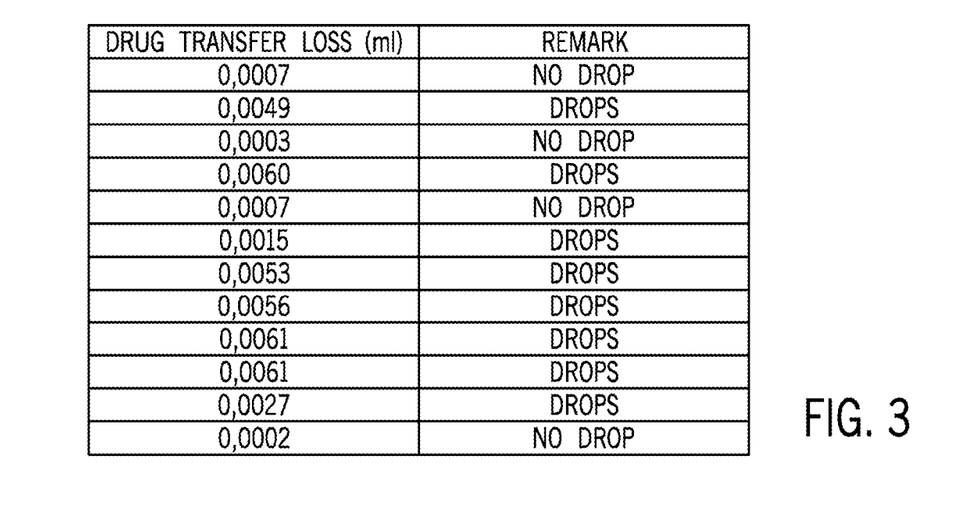

FIG. 3 shows measurements of drug transfer loss and correlation with observed loss of drops during drug transfer for select syringes used in the testing. The results show coherence between drops being lost and measured drug transfer loss. In one example, an average of the drug transfer losses from these samples may be used as DTL in Equation 1, which would be 0.00334 mL.

Figure 4:
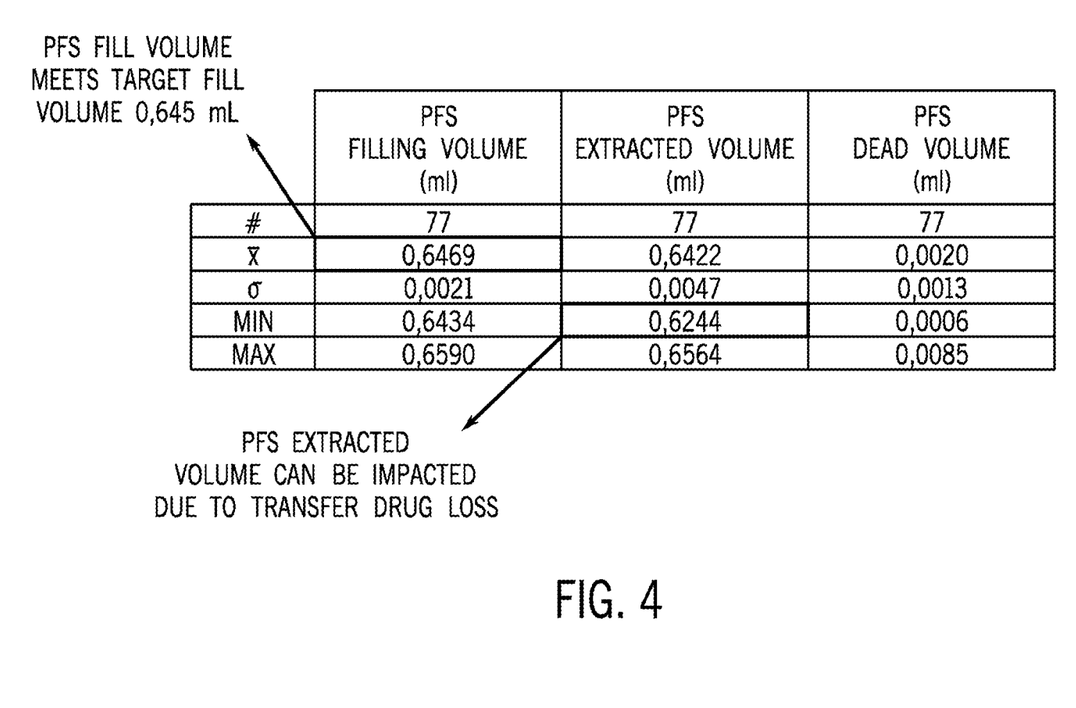

FIG. 4 shows results of measuring PFS filling volume, PFS extracted volume and PFS dead volume for 77 PFSs. On average, the PFSs were filled with 0.6469 mL. On average, 0.6422 mL was extracted, leaving 0.0047 mL unaccounted for. On average, PFS dead volume was 2.0 uL, as determined by measuring the weight of the PFSs before and after extraction. Subtracting the extracted volume and dead volume from the fill volume leaves on average 2.7 uL of drug transfer loss. Extractable PFS volume can be reduced by drug transfer loss.

Figure 5:
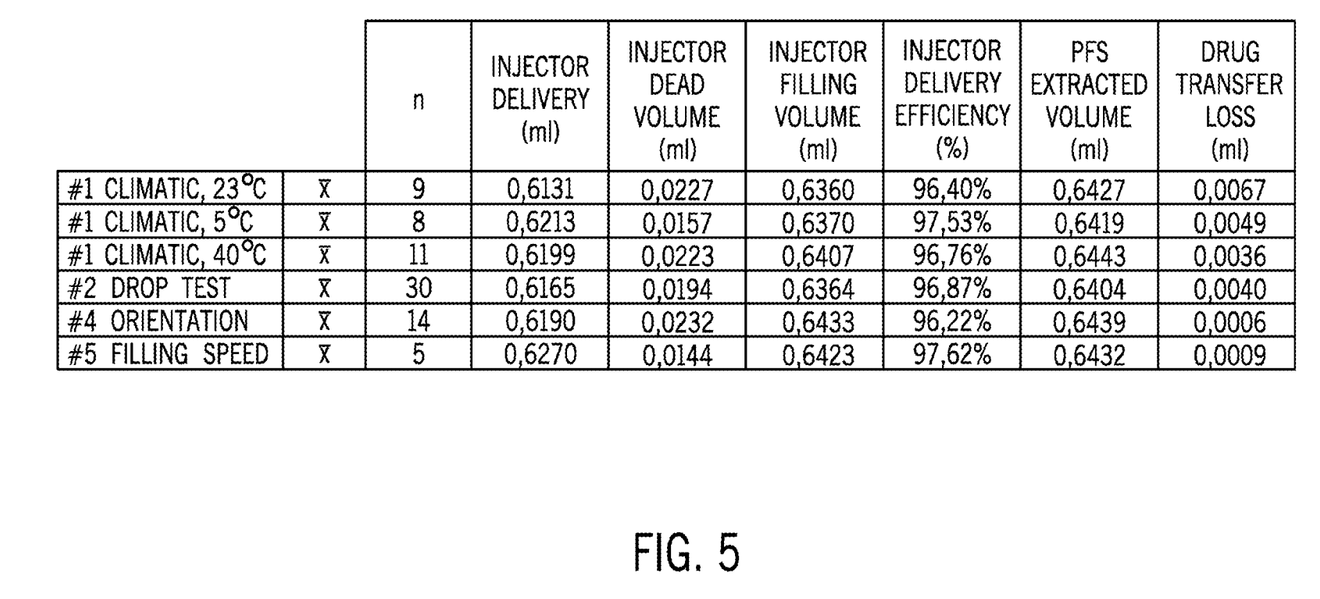

FIG. 5 shows an overview of results of tests #1, #2, #4 and #5. For example, in test #1, injectors were filled from PFSs at 23 degrees C. Volumes were measured at steps along the way from PFS extraction into injector and injector injection into target. With a sample size of 9, the average PFS extracted volume was 0.6427 mL and the average drug transfer loss was 0.0067 mL. As a result, the average injector filling volume was 0.6360 mL. Average injector volume delivered was 0.6131 mL and average injector dead volume was 0.0227 mL. Injector delivery efficiency was calculated based on $INJECTOR_{FV}/INJECTOR_{DV}*100$ to be 96.40%. Notably, for all tests shown in this chart, injector delivery efficiency was greater than 95%.

Figure 6:
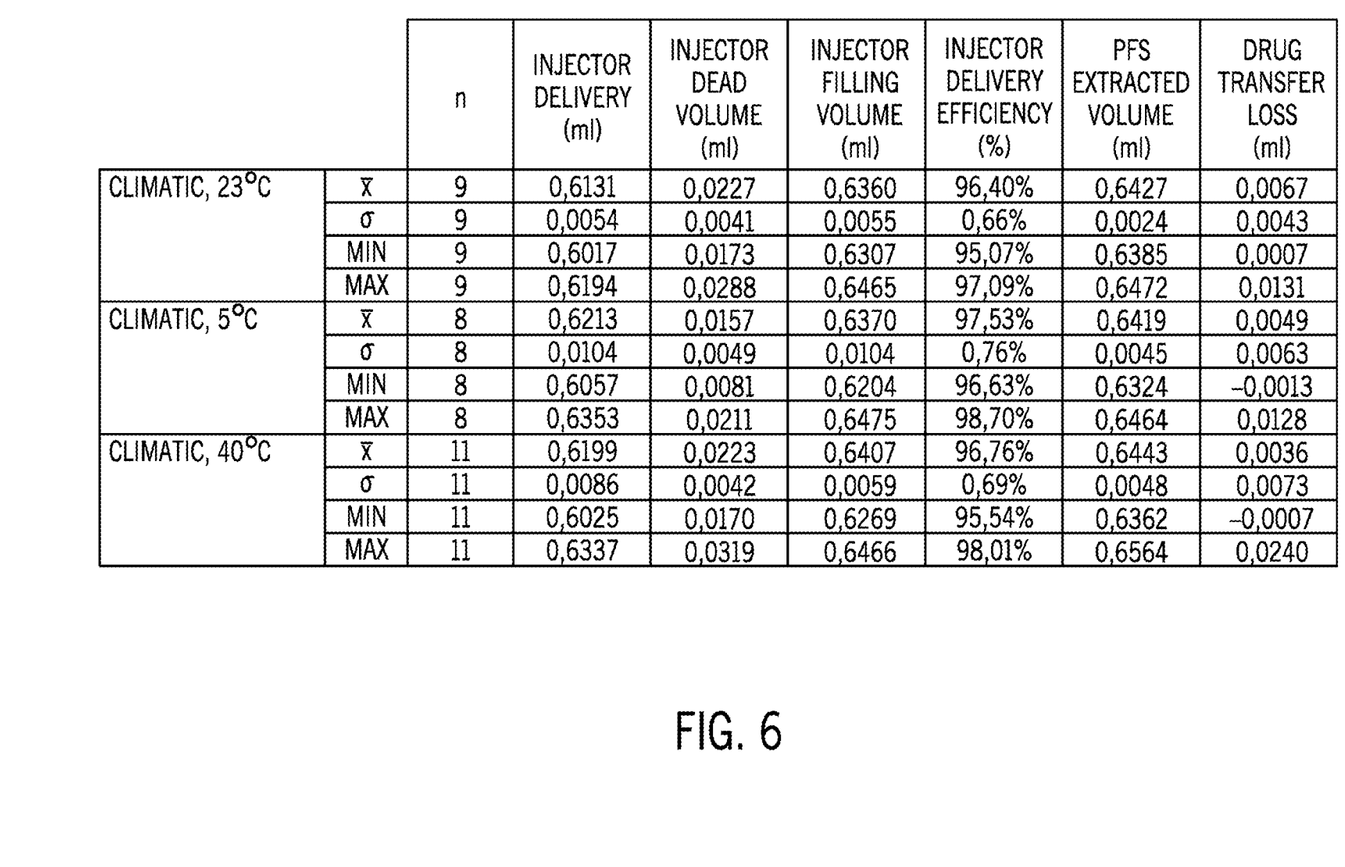

FIG. 6 is a table showing averages, standard deviations, minimums and maximums for the results of test #1. Injector devices were stored over dwell time and the injection was performed in different climatic conditions of 23 degrees C., 5 degrees C. and 40 degrees C. It was concluded that there was no significant temperature impact on injector dose accuracy or dose delivery efficiency. Average injector delivery volumes for the three climatic conditions were 0.6131 mL, 0.6213 mL and 0.6199 mL.

Figure 7:
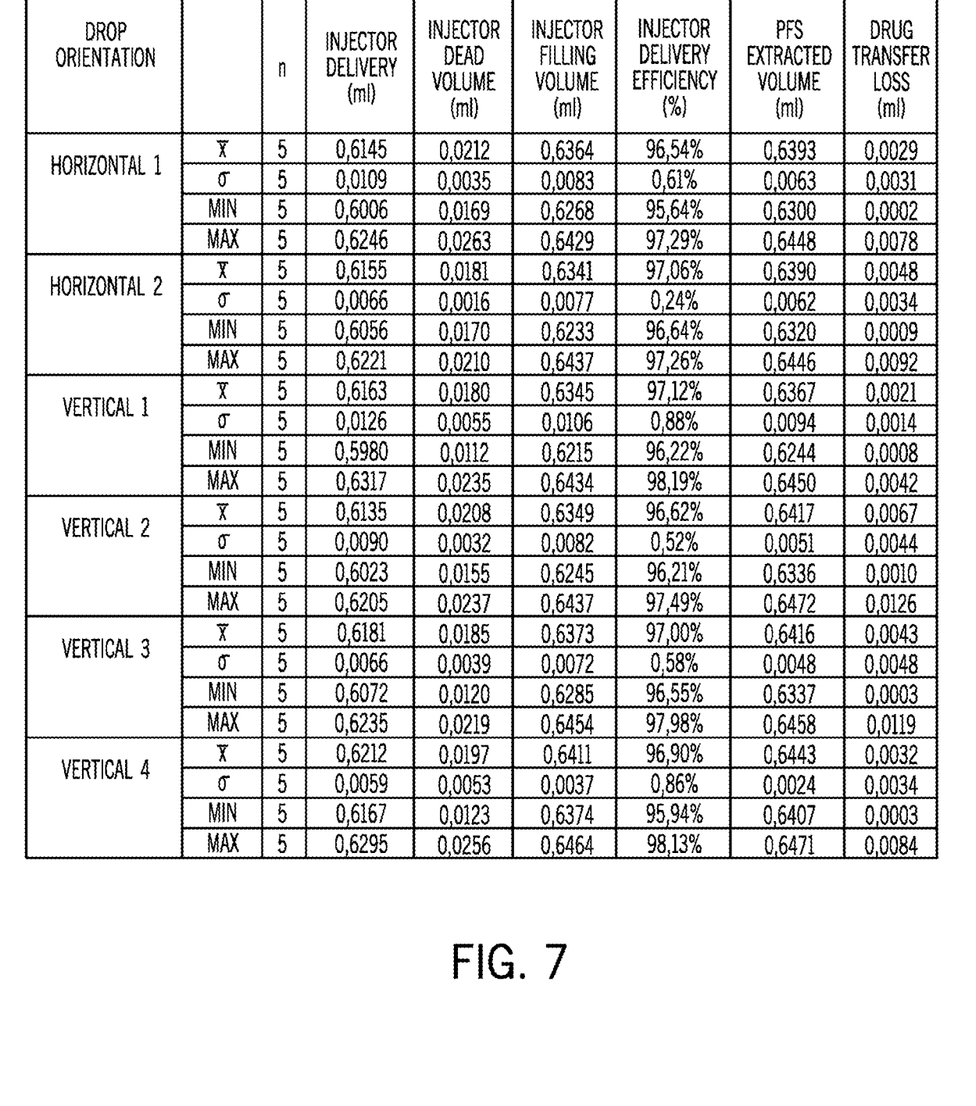

FIG. 7 is a table showing averages, standard deviations, minimums and maximums for the results of test #2. Injector devices were dropped before filling from different initial orientations. It was concluded that there were no obvious defects in the injector devices after dropping, that all had similar average delivered volumes, and that comparable injector device dose delivery efficiency was greater than 95%. Injector delivery volumes for the six orientations were 0.6145 mL, 0.6155 mL, 0.6163 mL, 0.6135 mL, 0.6181 mL, and 0.6212 mL.

Figure 8:
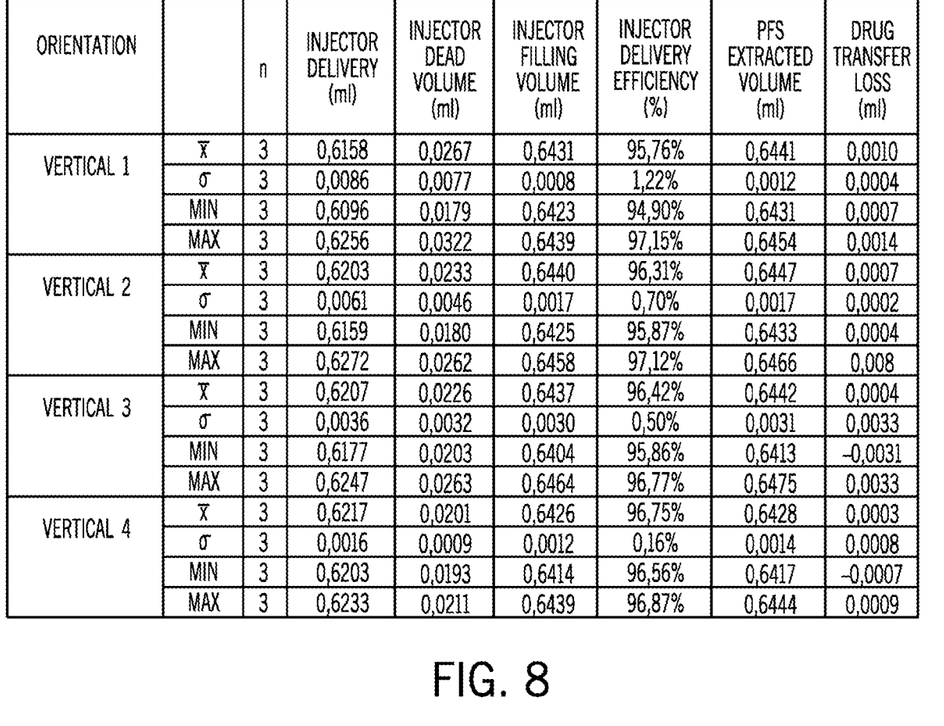

FIG. 8 is a table showing averages, standard deviations, minimums and maximums for the results of test #4. Injector devices were injected while being held in different orientations. It was concluded that no orientation was significantly problematic regarding injector dose delivery efficiency and that all orientations had injector device dose delivery efficiencies greater than 95%. Average injector delivery volumes for the four orientations were 0.6158 mL, 0.6203 mL, 0.6207 mL and 0.6217 mL.

Figure 9:
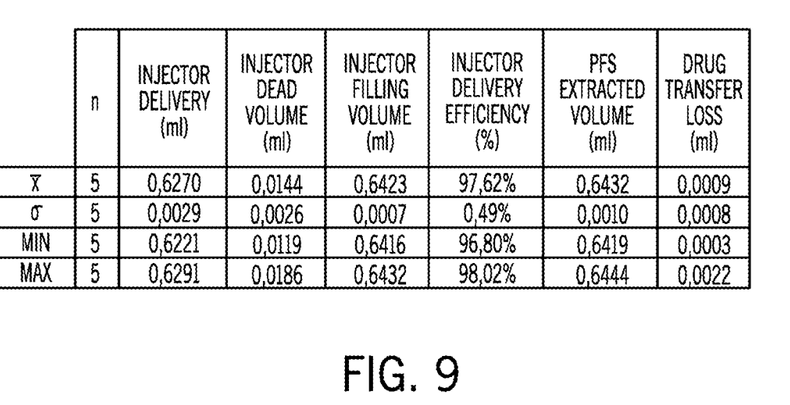

FIG. 9 is a table showing averages, standard deviations, minimums and maximums for the results of test #5, filling speed. In this test, the injector device was filled from the PFS as fast as manually possible by the person conducting the test. It was concluded that there was no negative impact of high filling speed on device functionality. Injector delivery volume was 0.6270 mL on average, minimum 0.6221 mL and maximum 0.6291 mL. Injector delivery efficiency was 97.62% on average.

Figure 10:
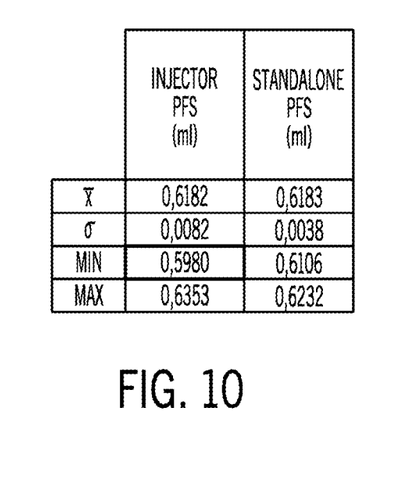
Figure 11:
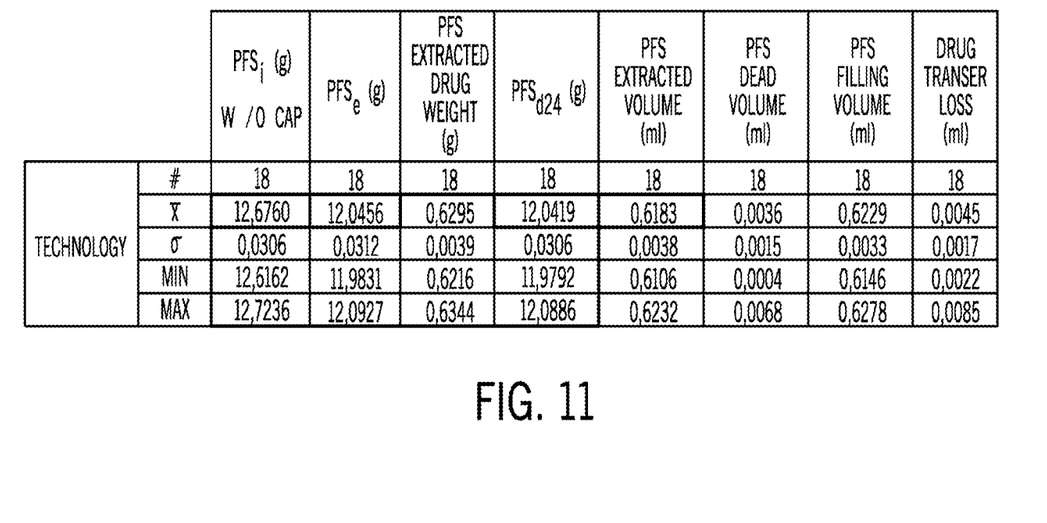

FIG. 10 is a table showing average injector delivery volume using the PFSs in the tests above of 0.6182 mL, with a standard deviation of 0.0082 mL, a minimum of 0.5980 mL and a maximum of 0.6353 mL. These numbers were compared to those for a standard PFS administration of pegfilgrastim without using an injector and with a different PFS initial volume designed to achieve a target dosage of 0.620 L. The sample size for the standard PFS volume test was 18. Results are shown in FIG. 11. The standard PFS administration had an average PFS extracted volume of 0.6183 mL, a standard deviation of 0.0038 mL, a minimum of 0.6106 mL and a maximum of 0.6232 mL.

Overall test delivered volume of injector PFS was 0.6182 mL on average and was determined to be comparable with administration by the standalone PFS to a patient (0.6183 mL). The minimum delivered volume of all tests was 0.5980 mL, which was below 0.6 mL. injector delivered volume at room temperature (23 degrees C.) was 0.6131 mL, which is 5 uL less than the standalone PFS. It was concluded that the filling volume of the PFS for injector use should be adjusted upward, for example from 0.645 mL to 0.650 mL. It was further concluded that filling volumes or initial PFS volumes of 0.645 mL to 0.650 mL would be suitable for use.

Figure 12A:
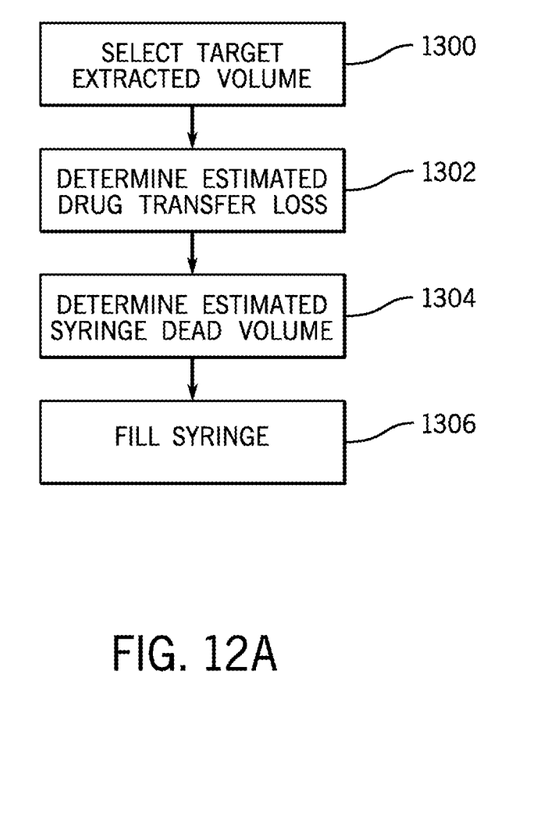
FIGS. 12A-12C are flowcharts of methods, according to illustrative embodiments.

Referring now to FIG. 12A, a method of filling a syringe with a pegfilgrastim solution will be described, according to an illustrative embodiment. The method may be used to provide a target extracted volume of pegfilgrastim solution from the syringe. For example, the target extracted volume may be 620 microliters of pegfilgrastim solution. The method may be used to fill a syringe with a volume of pegfilgrastim solution that will result in delivery of the target extracted volume, within a predetermined tolerance and/or within a predetermined confidence. For example, the method may provide syringes that will deliver 620 microliters+/− about 5, about 10 or about 20 microliters with a confidence of greater than 90%, greater than 95%, greater than 97%, etc. Sample sizes for determining the tolerance and/or confidence may comprise at least 10 samples, at least 20 samples, at least 50 samples, etc., in various embodiments. A standardized testing methodology and/or a testing methodology issued by a regulatory agency may be used to determine the tolerance and/or confidence.

At a block 1300, the method comprises selecting the target extracted volume of pegfilgrastim solution. In one embodiment, the target extracted volume of pegfilgrastim solution is 640 microliters to 644 microliters. In alternative embodiments, the target extracted volume of pegfilgrastim solution may comprise at least 640 microliters, at least 635 microliters, at least 620 microliters or other volumes. At a block 1302, the method comprises determining an estimated drug transfer loss, wherein drug transfer loss is the volume of pegfilgrastim solution lost after removal of a cap from the syringe and before the beginning of injection into a target. The determination can be made in any of a number of ways, such as empirical testing of a predetermined number samples, reference to a specification, etc. The syringe and/or cap may be weighed before and/or after cap removal, before and/or after priming, before and/or after alignment with the syringe needle facing downward, and/or before and/or after partial or complete injection of the contents of the syringe. An estimate can be determined by averaging the measured values from the samples, finding the mean, finding standard deviations, finding a range from maximum to minimum of the measured values, or using other statistical measures of estimation.

Referring to FIG. 12A, at a block 1304, the method comprises determining an estimated syringe dead volume, wherein the syringe dead volume comprises the volume of pegfilgrastim solution remaining in the syringe after completion of injection into the target. In some cases, the syringe dead volume may comprise the volume of pegfilgrastim solution plus the volume of gas remaining in the syringe after completion of injection into the target. The target may be a person, a device, or other target.

At a block 1306, the method comprises filling the syringe with a volume of pegfilgrastim solution comprising at least the target extracted volume plus the estimated drug transfer loss plus the estimated syringe dead volume, as shown in the Equation below.

$$\text{PFS FV} = \text{Volume\_to\_be\_injected} + \text{DTL} + \text{PFS}_{DV} \qquad \text{Equation 2}$$

The PFS volume may be, for example, 645 to 650 microliters inclusive, about 645 microliters (e.g., plus or minus about 1-2 microliters), about 650 microliters (e.g., plus or minus about 1-2 microliters), about 645 to about 650 microliters (e.g., plus or minus about 1-2 microliters), or other volumes. The volume filled may be absolute, as in the case of a single syringe, or an average fill volume of a batch of syringes, in which case individual syringes may be outside the specified volume filled but the syringes on average have the specified volume filled. In other embodiments, the volume filled may be a targeted or intended volume filled, reflecting a volume intended to be filled by the manufacturer.

In another embodiment, the syringe may be filled with this volume+$\text{INJECTOR}_{DV}$, as in Equation 1 above.

In another embodiment, the estimated syringe gas volume may be determined, and the estimated syringe gas volume may be subtracted from the volume of pegfilgrastim solution that is filled into the syringe. The gas volume, like the dead volume, may be measured empirically using a predetermined number of samples. The determination may also be estimated based on the surface tension of the pegfilgrastim solution, the surface tensions of the materials enclosing the dead volumes, the speed of injection/flushing of liquid through the dead volumes, and/or other factors.

According to another embodiment, a method of making a prefilled syringe comprises providing a syringe having a barrel and filling the barrel with a pegfilgrastim solution to a volume of 645 microliters to 650 microliters. The pegfilgrastim solution may be a solution comprising pegfilgrastim, such as that described herein comprising about 10 mg/ml pegfilgrastim, 10 mM acetate, 5 wt. % sorbitol and 0.0004 wt. % polysorbate 20. The barrel may be filled from either end. The dispensing end may comprise a narrowed portion configured to hold a needle, or it may be configured as a Luer connection or other connection. A stopper or seal and plunger may also be coupled to the barrel before or after the filling with pegfilgrastim solution. In some cases, the fill volume of the syringe must be precise to ensure the output volume too is precise. In some cases, if the output volume is incorrect by even a small amount, it can lead to a failure of a pharmacodynamic/pharmacokinetic study and/or in treatment result. In some cases, an imprecise dosage can have a disproportionately different impact on a patient.

As mentioned, the barrel may be filled with 645 microliters to 650 microliters, inclusive. In one embodiment, the barrel is filled with about 650 microliters (+/−about 1 or 2 microliters) of the pegfilgrastim solution. In another embodiment, the barrel is filled with about 645 microliters (+/−about 1 or 2 microliters) of the pegfilgrastim solution. In some embodiments, the syringe may have a dead volume of between 0.6 and 8.5 microliters, which may be measured empirically (e.g., weighing a number of syringes, such as at least 10, at least 20, etc. and averaging), theoretically (by calculating volumes of dead volume in the syringe, estimating based on surface tension of syringe parts and pegfilgrastim solution, considering impact of speed of dispensing, etc.), or in other ways. In some embodiments, the syringe has a dead volume of about 2 microliters.

In another embodiment, a method of filling a device from a prefilled syringe comprises providing a prefilled syringe having a barrel, stopper and plunger, the barrel containing 645 to 650 microliters of pegfilgrastim solution. The method further comprises moving the plunger and stopper to expel the pegfilgrastim solution into the device. In some embodiments, at least 624 microliters are expelled into the device to provide a sufficient amount to obtain a desired PK/PD response in a patient. In some embodiments, at least 642 microliters are expelled into the device to obtain a desired PK/PD response in a patient. The difference in volume can be attributable to differences in the pegfilgrastim solution, differences in the loss attributed to the device before the solution reaches a patient, etc. In another embodiment, between 624 microliters and 650 microliters are expelled into the device. In some embodiments, the prefilled syringe may have a dead volume of at least 0.6 microliters and/or 8.5 microliters or less.

In another embodiment, a prefilled syringe may comprise a barrel containing 645 microliters to 650 microliters of a pegfilgrastim solution, a plunger and a stopper slidably disposed in the barrel. The pegfilgrastim solution may be an aqueous solution comprising about: 10 mg/ml pegfilgrastim, 10 mM acetate, 5 wt. % sorbitol, and 0.0004 wt. % polysorbate 20. In some embodiments, the barrel contains about 650 microliters of the pegfilgrastim solution (e.g., +/−about 1-2 microliters for the barrel or averaged over a batch of barrels manufactured). In some embodiments, the syringe has a dead volume of at least 0.6 microliters and/or 8.5 microliters or less. In some embodiments, the syringe has a dead volume of about 2 microliters. In some embodiments, the syringe is configured to expel at least 624 microliters of the pegfilgrastim solution, again in the particular syringe or averaged over a batch of manufactured syringes. In some embodiments, the syringe is configured to expel at least 642 microliters of the pegfilgrastim solution. In some embodiments, the syringe is configured to expel between 624 microliters and 650 microliters of the pegfilgrastim solution.

In another embodiment, a prefilled syringe comprises a barrel containing a pegfilgrastim solution, a plunger, and a stopper disposed in the barrel and configured to be moved from a first position to a terminal position by the plunger, wherein movement of the stopper from the first position to the terminal position expels between 640 microliters and 656 microliters of the pegfilgrastim solution. The first position can be a position in which the plunger is disposed upon removing the syringe from a packaging for sale or delivery. The first position may alternatively be a position of the stopper after a clinician has primed the syringe or otherwise removed air bubbles. The first position may be other positions of the plunger within the barrel. The terminal position is the position approximately at the end of travel of the plunger within the barrel toward an outlet end. The terminal position would typically be reached by a clinician pressing the plunger all the way until it stops. In this embodiment, the prefilled syringe may be filled with more than 640 microliters and/or more than 656 microliters (e.g., 670, 680, 700 microliters, etc.), but the structure of the prefilled syringe is configured to expel only between 640 microliters and 656 microliters. In some cases, the syringe may be designed to retain a volume of pegfilgrastim solution beyond what would typically occupy the dead volume, e.g., 10, 25, 40 microliters, etc. The barrel may be filled with 645 to 650 microliters of pegfilgrastim, about 645 microliters, or about 650 microliters. In some embodiments, movement of the stopper from the first position to the terminal position expels 645 microliters to 650 microliters of the pegfilgrastim solution. In some embodiments, the prefilled syringe has a dead volume of between 0.6 and 8.5 microliters. In some embodiments, prefilled syringe has a dead volume of about 2 microliters.

In the various embodiments described herein, one or more of the aspects of one embodiment may be employed along with a different embodiment to create yet another embodiment.

Figure 12B:
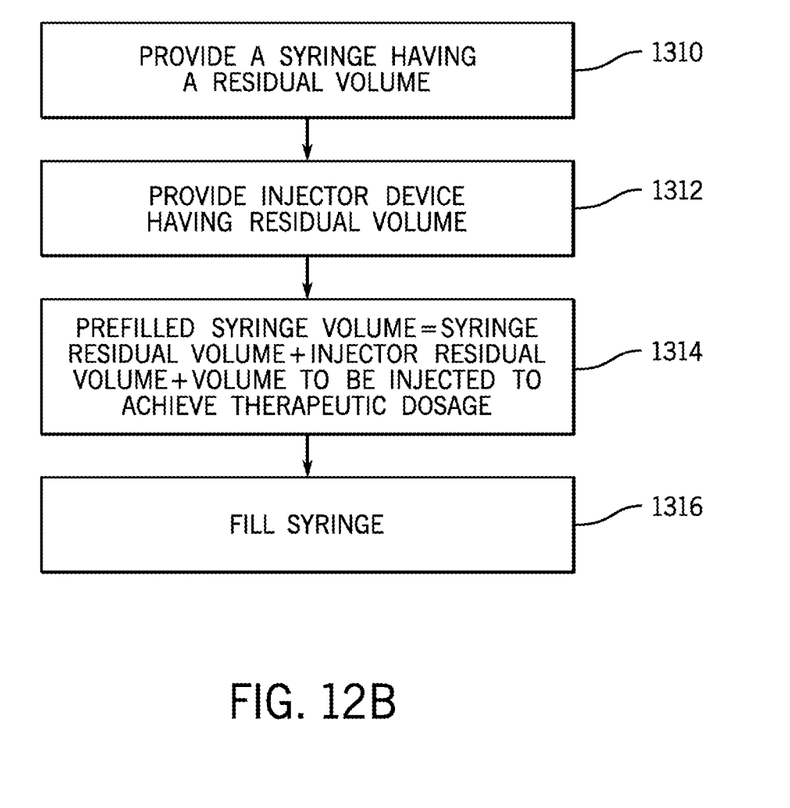

Referring now to FIG. 12B, a method of filling a syringe with a pegfilgrastim solution will be described, according to an illustrative embodiment. The syringe may be filled with a volume to ensure a therapeutic dosage of pegfilgrastim is delivered to a patient by an injector device. At a block 1310, the method comprises providing a syringe having a residual volume. The syringe residual volume may represent an amount of pegfilgrastim solution that remains in the syringe, for a specific syringe or on average in a batch of syringes manufactured, after a clinician thrusts the plunger to a terminal position while expelling the pegfilgrastim solution into the injector. At a block 1312, the method comprises providing an injector device having an injector residual volume. The injector residual volume may represent an amount of pegfilgrastim solution that remains in the injector, for a specific injector or on average in a batch of injectors manufactured, after an injector completes an injection operation on a patient.

At a block 1314, a prefilled syringe volume is determined to be the sum of the syringe residual volume, the injector residual volume and a volume to be injected to achieve the therapeutic dosage of pegfilgrastim. At a block 1316, the method comprises filling the syringe with a prefilled syringe volume of the pegfilgrastim solution.

In one embodiment, the residual volume in the syringe is at least about 0.7 microliters and/or about 4.9 microliters or less. In another embodiment, the residual volume in the injector device is at least about 14.4 microliters and/or about 23.2 microliters or less.

In another embodiment, the prefilled syringe volume further comprises the sum of a drug transfer loss, summed with the other factors described above.

The syringe residual volume may be a dead volume of the syringe minus a volume of gas left in the syringe.

The injector residual volume may be a dead volume for the injector minus a volume of gas left in the injector.

According to another embodiment, a pegfilgrastim solution kit may comprise an injector and a prefilled syringe filled with 645 microliters to 650 microliters of a pegfilgrastim solution. The PFS and injector may be packaged within a single package or may be packaged in separate packages but sold together as a kit. In some embodiments, the injector has a dead volume of about 14.4 microliters to about 23.2 microliters. In some embodiments, the injector has a dead volume of more than 20 microliters. In some embodiments, the prefilled syringe has a dead volume of 0.6 to 8.5 microliters. In some embodiments, the prefilled syringe has a dead volume of about 2 microliters. In some embodiments, a delivery efficiency of the injector is at least 95%, again for a specific injector or on average over a batch of injectors manufactured. In some embodiments, the injector comprises an adhesive lower surface for attachment to the skin of a patient and a reservoir configured to hold a volume of the pegfilgrastim solution when injected from the prefilled syringe into the injector.

Figure 12C:
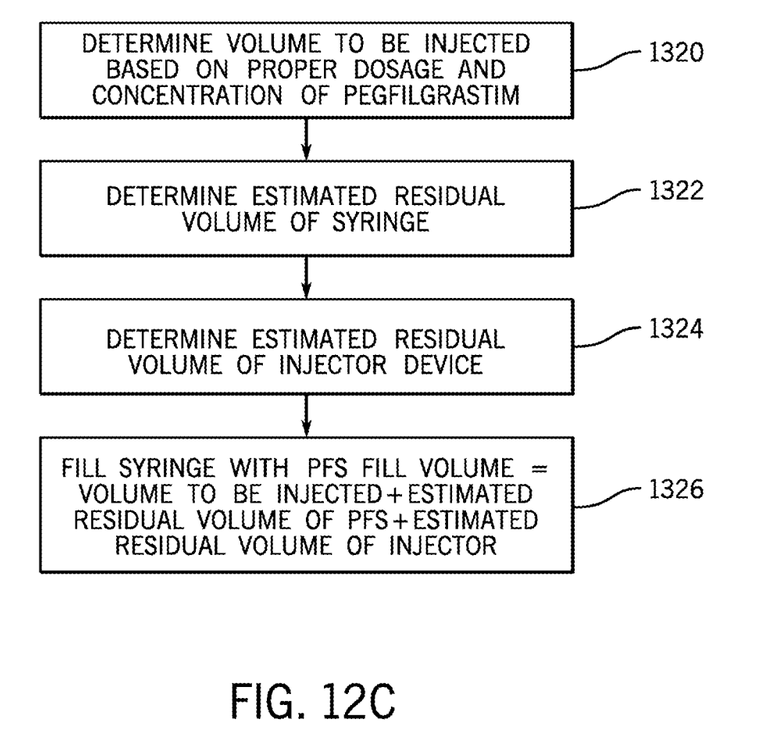

Referring now to FIG. 12C, a method of filling a syringe with pegfilgrastim will be described. In this method, the objective is to provide a proper dosage of pegfilgrastim to a patient by an injector device. At a block 1320, the method comprises determining a volume to be injected based on proper dosage and concentration of pegfilgrastim. For example, the volume to ensure a therapeutic dosage of 6 mg/0.6 mL pegfilgrastim is delivered to a patient may be about 600 microliters, about 620 microliters, etc., and may be understood to have a predetermined tolerance and/or predetermined confidence over a certain number of samples. At a block 1322, the method comprises determining an estimated residual volume in the syringe, which can be done by various techniques, such as empirical studies, measuring, estimating, etc. At a block 1324, the method comprises determining an estimated residual volume in the injector device. At a block 1324, the method comprises determining a prefilled syringe fill volume by adding the volume to be injected to the estimated residual volume in the prefilled syringe and the estimated residual volume in the injector device. This determination can of course be done once for the manufacture of many syringes. At a block 1326, the method comprises filling the syringe with the prefilled syringe fill volume of the pegfilgrastim solution. In some embodiments, the therapeutic dosage is about 600 microliters. In some embodiments, the therapeutic dosage is about 620 microliters. In some embodiments, the estimated residual volume in the syringe is at least about 0.7 microliters and/or about 4.9 microliters or less. In some embodiments, the estimated residual volume in the injector device is at least about 14.4 microliters and/or about 23.2 microliters or less. In some embodiments, the prefilled syringe volume further comprises the sum of a drug transfer loss. In some embodiments, the syringe residual volume is a dead volume of the syringe minus a volume of gas left in the syringe. In some embodiments, the injector residual volume is a dead volume for the injector minus a volume of gas left in the injector.

While the specification describes methods and devices for filling injector devices with pegfilgrastim, the teachings herein may be used to implement methods for filling injector devices and syringes containing other liquids, such as solutions, which may comprise any of adalimumab, rituximab, risankizumab, etanercept, trastuzumab, ado-trastuzumab emtansine, trastuzumab deruxtecan, bevacizumab, infliximab, pegfilgrastim, filgrastim, tocilizumab, golimumab, interferon beta-la, ranibizumab, denosumab, pembrolizumab, nivolumab, aflibercept, eculizumab, ocrelizumab, pertuzumab, secukinumab, omalizumab, ustekinumab, vedolizumab, daratumumab, dupilumab, atezolizumab, natalizumab, bortezomib, ipilimumab, durvalumab, emicizumab, palivizumab, guselkumab, mepolizumab, panitumumab, ramucirumab, belimumab, abatacept, certolizumab pegol, ixekizumab, romiplostim, benralizumab, evolocumab, canakinumab, obinutuzumab, cetuximab, erenumab, blinatumomab, romosozumab, mirikizumab, inotuzumab, sacituzumab govitecan, enfortumab vedotin, or brentuximab vedotin.

While in some embodiments the volumes of 645 microliters to 650 microliters of pegfilgrastim solution are described herein, these volumes may vary in different embodiments based on concentration of pegfilgrastim, size of reservoir, type or characteristics of PFS, type or characteristics of injector, etc. For example, the initial volume for the prefilled syringe may be at least 600 microliters, at least 610 microliters, at least 620 microliters, at least 630 microliters, at least 640 microliters, at least 650 microliters, at least 660 microliters, at least 670 microliters, etc. The initial volume of the prefilled syringe may be 670 microliters or less, 660 microliters or less, 650 microliters or less, 640 microliters or less, 630 microliters or less, 620 microliters or less, 610 microliters or less, or 600 microliters or less.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A method of filling a device from a prefilled syringe, comprising:
   providing a prefilled syringe having a barrel, stopper and plunger, the barrel containing 645 to 660 microliters of pegfilgrastim solution, wherein the prefilled syringe has a dead volume of 0.6 microliters to 8.5 microliters; and
   moving the plunger and stopper to expel the pegfilgrastim solution into the device.

2. The method of claim 1, wherein at least 624 microliters are expelled into the device.

3. The method of claim 2, wherein at least 642 microliters are expelled into the device.

4. The method of claim 1, wherein between 624 microliters and 650 microliters are expelled into the device.

5. The method of claim 1, wherein the barrel contains 645 to 650 microliters of the pegfilgrastim solution.

* * * * *